(12) United States Patent
Suemasa (10) Patent No.: US 11,961,230 B2
(45) Date of Patent: Apr. 16, 2024

(54) DISCERNING DEVICE, CELL MASS DISCERNING METHOD, AND COMPUTER PROGRAM

(71) Applicant: JSR Corporation, Tokyo (JP)

(72) Inventor: Daichi Suemasa, Tokyo (JP)

(73) Assignee: JSR Corporation, Tokyo (JP)

( * ) Notice: Subject to any disclaimer, the term of this patent is extended or adjusted under 35 U.S.C. 154(b) by 381 days.

(21) Appl. No.: 17/304,877

(22) Filed: Jun. 28, 2021

(65) Prior Publication Data

US 2021/0327060 A1 Oct. 21, 2021

Related U.S. Application Data

(63) Continuation of application No. PCT/JP2019/044456, filed on Nov. 13, 2019.

(30) Foreign Application Priority Data

Jan. 23, 2019 (JP) .................................. 2019-009384

(51) Int. Cl.
*G06T 7/00* (2017.01)
*C12M 1/32* (2006.01)
*C12M 1/34* (2006.01)

(52) U.S. Cl.
CPC ........... *G06T 7/0012* (2013.01); *C12M 23/12* (2013.01); *C12M 41/36* (2013.01); *G06T 2207/20081* (2013.01); *G06T 2207/30024* (2013.01)

(58) Field of Classification Search
None
See application file for complete search history.

(56) References Cited

U.S. PATENT DOCUMENTS 11,725,184 B2 * 8/2023 Ortega ................. A61K 35/407
424/93.7
2014/0243227 A1 * 8/2014 Clevers ................ C12N 5/0679
506/10

(Continued)

FOREIGN PATENT DOCUMENTS

EP 3 530 725 A1 8/2019
JP 2014-516562 A 7/2014

(Continued)

OTHER PUBLICATIONS

International Search Report dated Feb. 10, 2020 in PCT/JP2019/044456 filed on Nov. 13, 2019, 4 pages (with English Translation).

(Continued)

*Primary Examiner* — Delomia L Gilliard
(74) *Attorney, Agent, or Firm* — Oblon, McClelland, Maier & Neustadt, L.L.P.

(57) ABSTRACT

A discerning device that discerns a cell mass includes: a storage unit that stores a trained model that has been subjected to machine learning on the basis of training data in which an index associated with a first cell mass out of a predetermined index including at least one index indicating a feature of a cell mass is correlated with information indicating whether a state of the first cell mass is a first state or a second state that is different from the first state; an image-analyzing unit that acquires an index associated with a second cell mass out of the predetermined index; and a discerning-processing unit that discerns whether a state of the second cell mass is the first state or the second state on the basis of the index associated with the second cell mass and the trained model.

13 Claims, 6 Drawing Sheets

(56) References Cited

U.S. PATENT DOCUMENTS

2021/0287373 A1* 9/2021 Murata .............. H04N 1/00167
2021/0327060 A1* 10/2021 Suemasa ................ C12M 41/48

FOREIGN PATENT DOCUMENTS

| JP | 2019-000014 A | 1/2019 |
| WO | WO 2012/168930 A2 | 12/2012 |
| WO | WO 2018/083984 A1 | 5/2018 |
| WO | WO 2019/009420 A1 | 1/2019 |

OTHER PUBLICATIONS

Borten et al., "Automated brightfield morphometry of 3D organoid populations by OrganoSeg", Scientific Reports, Nature, s41598-017-18815-8, 8:5319, 2018, 10 pages.

* cited by examiner

| File Name | A1each001.jpg |
|---|---|
| Parent File Name | A1.jpg |
| Size | 399.5 |
| Circularity | 0.85 |
| Aspect | 166 |
| Roughness | 1.32 |
| Budding Rate | 22 |

| File Name | A1.jpg |
|---|---|
| Size | 763 |
| Sigma | 559.33 |
| Number | 38 |
| Budding Rate | 0.41 |

DISCERNING DEVICE, CELL MASS DISCERNING METHOD, AND COMPUTER PROGRAM

CROSS-REFERENCE TO RELATED APPLICATIONS

The present application is a continuation application of International Application No. PCT/JP2019/044456, filed Nov. 13, 2019, which claims priority to Japanese Patent Application No. 2019-009384, filed Jan. 23, 2019. The contents of these applications are incorporated herein by reference in their entirety.

BACKGROUND OF THE INVENTION

Field of the Invention

The present invention relates to a discerning device, a cell mass discerning method, and a computer program.

Description of the Related Art

Recently, culture of organoids which are three-dimensional structures that are very similar to tissue or internal organs of a living body has been studied. For example, Non-Patent Literature 1 (M. A. Borten, et al., "Automated brightfield morphometry of 3D organoid populations by OrganoSeg", Scientific Reports, s41598-017-18815-8, Nature, 28 Mar. 2018) discloses a technique for classifying phenotypes by extracting features from an image of cultured organoids and analyzing the extracted features. By analyzing cultured organoids, for example, it is possible to more accurately ascertain various physiopathological conditions such as those of tissue regeneration, stem cells, functions of stem cell niches, tissue reactions to drugs, and mutation or tissue damage.

By the way, only organoids which have grown normally have to be used for organoid analysis. In order to efficiently culture normal organoids, it is preferable to accurately discern whether or not a cell mass is a precursor of an organoid at the stage of growth, and to select only a precursor expected to be an organoid in advance.

However, in the related art, for example, in the culture of intestinal organoids, whether or not a cell mass is a precursor of an organoid is often discerned on the basis of determination by an expert's eyes. Accordingly, there is a problem in that discernment is not be able to be performed unless there is an expert. Furthermore, since the discernment is based on qualitative determination by an expert, there is a problem in that discrepancies may occur between discernment results. By the way, when drug screening using organoids is performed, it is conceivable that a large number of organoids will be used. Since reproducibility of results or stability of sensitivity to a specific drug is required for drug screening, homogeneous organoids are necessary. Accordingly, organoids with stable quality are necessary as organoids used for drug screening, and thus there is demand for a technique for quantitatively discerning whether or not a cell mass is a precursor of an organoid regardless of a difference in technique between experts or the like.

SUMMARY OF THE INVENTION

The present invention was contrived in consideration of the aforementioned technical circumstances and an objective thereof is to provide a technique for quantitatively discerning whether or not a cell mass is a precursor of an organoid.

An aspect of the present invention is the above discerning device, and the first state is a budding state and the second state is a cyst state.

An aspect of the present invention is the above discerning device, and the predetermined index includes an index indicating darkness of the cell mass.

An aspect of the present invention is the above discerning device, and the predetermined index includes an index indicating complexity of a shape of the cell mass.

An aspect of the present invention is the above discerning device, and the machine learning is learning to determine a partial regression coefficient of a logistic function with the predetermined index as an explanatory variable.

An aspect of the present invention is the above discerning device and further includes an image-acquiring unit that transmits an image in which the second cell mass is captured to the image-analyzing unit.

An aspect of the present invention is the above discerning device, and the image-analyzing unit detects edges of the second cell mass from the image using the Canny method and measures an index indicating complexity of a shape of the cell mass on the basis of the number of detected edges.

An aspect of the present invention is a discerning method of a cell mass that is performed by a computer, and the discerning method includes: a step of acquiring a trained model that has been subjected to machine learning on the basis of training data in which an index associated with a first cell mass out of a predetermined index including at least one index indicating a feature of a cell mass is correlated with information indicating whether a state of the first cell mass is a first state or a second state that is different from the first state; a step of acquiring an index value associated with a second cell mass out of the predetermined index; and a step of discerning whether a state of the second cell mass is the first state or the second state on the basis of the acquired index associated with the second cell mass and the trained model.

An aspect of the present invention is a computer program including an instruction for causing a computer to execute the discerning method of the cell mass according to claim 8 at a time of execution in the computer.

The discerning device according to the aspects of the present invention can quantitatively discern whether or not a cell mass is a precursor of an organoid.

DESCRIPTION OF EMBODIMENTS

Hereinafter, an embodiment of the present invention (hereinafter also referred to as "the present embodiment") will be described with reference to the accompanying drawings, but the present invention is not limited to the following embodiment at all.

A discerning device according to the present embodiment described below is a device that discerns whether or not a cell mass for culturing an organoid is a precursor of an organoid on the basis of a growing state of the cell mass. First, culture of organoids and a flow of the above discerning according to the present embodiment will be described.

Figure 1:
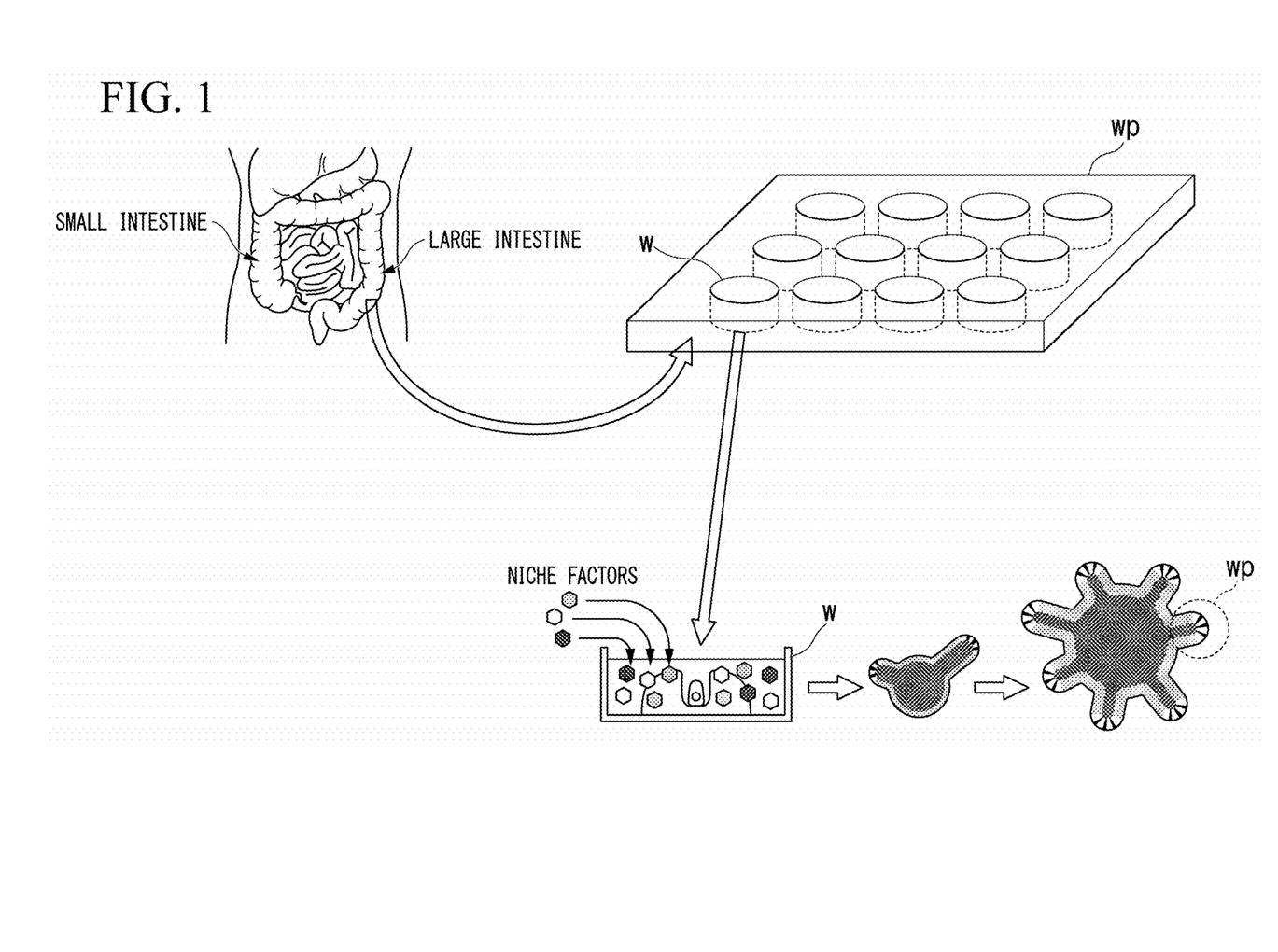
FIG. 1 is a diagram schematically illustrating a flow of culture of organoids.

FIG. 1 is a diagram schematically illustrating a flow of culture of organoids. First, culture media including niche factors are prepared in advance in a plurality of (12 in the example illustrated in FIG. 1) wells w included in a well plate wp. Then, a cell mass (for example, a cell mass including intestinal epithelial stem cells) is input into each well w. Accordingly, a cell mass grows in each well w and culture of an organoid is performed. A plurality of cell masses which are to be organoids may be present in one well w.

The inside of each well w can be imaged by an imaging device (not illustrated). A captured image is divided in units of cell masses and each divided image is an image to be analyzed (hereinafter referred to as an "analysis target image"). An example of a specific method of dividing an image is as follows. First, a plurality of ranges corresponding to a cell mass which is to be an organoid are recognized as a plurality of regions of interest (ROIs) in a captured image in each well w. This is performed, for example, by setting an appropriate threshold value using an OpenCV-Python library. Then, a plurality of analysis target images are generated by dividing the image to correspond to the recognized ROIs.

The discerning device acquires an analysis target image and an image-analyzing unit performs image analysis of the analysis target image. In the image analysis, for example, five indices illustrated in FIG. 2 are measured for the analysis target image.

Figure 2:
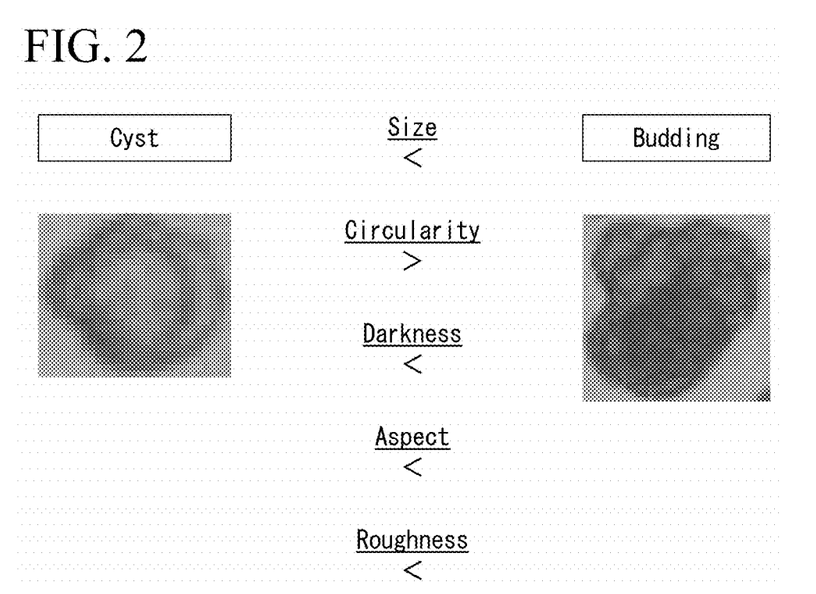
FIG. 2 is a diagram describing five indices used by a discerning device according to an embodiment of the present invention.

FIG. 2 illustrates an example of indices used for image analysis. As illustrated in FIG. 2, in image analysis, five indices including Size, Circularity, Darkness, Aspect, and Roughness are measured and analyzed for a cell mass appearing in the acquired analysis target image. Then, the image-analyzing unit discerns whether or not the cell mass appearing in the analysis target image is a precursor of an organoid on the basis of the measured indices.

In general, it is known that a cell mass can be discerned as a precursor of an organoid on the basis of an appearance of budding (hereinafter referred to as a "budding state"). When a cell mass is a precursor of an organoid, the cell mass is characterized in that tissue with a ruffled (pleated) structure grows and a shape thereof becomes complex, and thus discerning can be performed on the basis of such characteristics. The five indices described above are, for example, indices selected on the basis of such characteristics of an intestinal organoid.

The image-analyzing unit performs image analysis to determine whether the state of the cell mass is a budding state or a cyst state, which corresponds to a state opposite to the budding state, (that is, whether or not the cell mass appearing in the analysis target image is a precursor of an organoid) on the basis of the measured five indices.

Specifically, the image-analyzing unit calculates a value of a budding rate indicating a probability of the budding state by inputting the five indices to a trained model generated through machine learning in advance. A discerning-processing unit discerns whether the state of the cell mass is the budding state or the cyst state on the basis of the value of the budding rate. It should be noted that the discerning-processing unit discerns whether the state of the cell mass is the budding state or the cyst state, for example, on the basis of whether or not the value of the budding rate exceeds a predetermined threshold value.

For example, the following measuring method is used as a specific method of measuring the five indices.

Measurement of the Size is performed, for example, by measuring the number of pixels in an area corresponding to an ROI of an analysis target image. That is, the Size is an index indicating the size of a cell mass. In general, since a precursor of an organoid increases in size, the state of a cell mass is more likely to be discerned to be in the budding state as the value of a Size thereof increases.

Measurement of the Circularity is performed, for example, by calculating Expression (1) described below.

$$\text{Circularity} = 4\pi S/(\text{Per})^2 \qquad (1)$$

Here, S represents a diameter (or a radius) of an ROI of an analysis target image. Moreover, Per represents a length of a circumference of the ROI of the analysis target image. That is, the Circularity is a parameter representing to what extent the shape of a cell mass is similar to a circle. The Circularity is expressed as a value from 0 to 1 by Expression (1). For example, when the shape of the outer circumference of the cell mass is a perfect circle, the value of the Circularity is 1. On the other hand, as the shape of the outer circumference of the cell mass becomes more complex, the value of the Circularity becomes closer to 0. In general, since the shape of the outer circumference of a precursor of an organoid grows complex, the state of the cell mass is more likely to be discerned to be in the budding state as the value of the Circularity becomes smaller.

Measurement of the Darkness is performed, for example, by calculating Expression (2) described below.

$$\text{Darkness} = B_o - B_i \qquad (2)$$

Here, $B_o$ represents an average value of luminance (for example, of 256 gray scales) around an ROT. Moreover, $B_i$ represents an average value of luminance (for example, of 256 gray scales) inside the ROT (that is, inside a cell mass). That is, the Darkness is expressed by a difference between the luminance inside the ROT and the luminance around the ROT. In general, a precursor of an organoid grows three-dimensionally such that a thickness thereof increases. Accordingly, since a transmittance of light inside the ROT decreases, the state of the cell mass is more likely to be discerned to be in the budding state as the value of the Darkness becomes larger.

Measurement of the Aspect is performed, for example, by measuring a longest axis (a major axis) and a shortest axis (a minor axis) of an ROT included in an analysis target image and dividing the length of the longest axis by the length of the shortest axis. That is, the value of the Aspect is calculated, for example, by an expression of Aspect=length of longest axis/length of shortest axis. In general, since a precursor of an organoid grows such that a shape thereof becomes complex, in the case of an intestinal organoid, the state of a cell mass is more likely to be discerned to be in the budding state as the value of the Aspect becomes larger.

Measurement of the Roughness is performed, for example, by detecting edges of an ROT and measuring the number of detected edges. For example, a technique such as the Canny method can be used to detect edges. In general, since a precursor of an organoid grows such that a shape thereof becomes complex, the state of a cell mass is more likely to be discerned to be in the budding state as the value of the Roughness becomes larger.

It should be noted that in FIG. 2, the five indices described above are used, but the present invention is not limited thereto and the number of indices used is arbitrary. It is predicted that as the number of indices used becomes larger, it will be possible to more accurately discern whether or not a precursor which appears in an analysis target image is a precursor that grows into a normal organoid, but it is predicted that costs associated with measurement of the indices or the like will further increase.

It should be noted that the indices illustrated in FIG. 2 are selected as useful indices to discern whether or not a cell mass is a precursor of an intestinal organoid. Accordingly, when an organ of which an organoid is to be cultured is, for example, an organ other than an intestine, suitable indices for the organ or the like to be cultured can be selected. It should be noted that when it is discerned whether or not a cell mass is a precursor of an intestinal organoid, it is particularly preferable to seriously consider the indices of Darkness and Roughness.

[Functional Configuration of Discerning Device]

A functional configuration of the discerning device according to the present embodiment will be described below.

Figure 3:
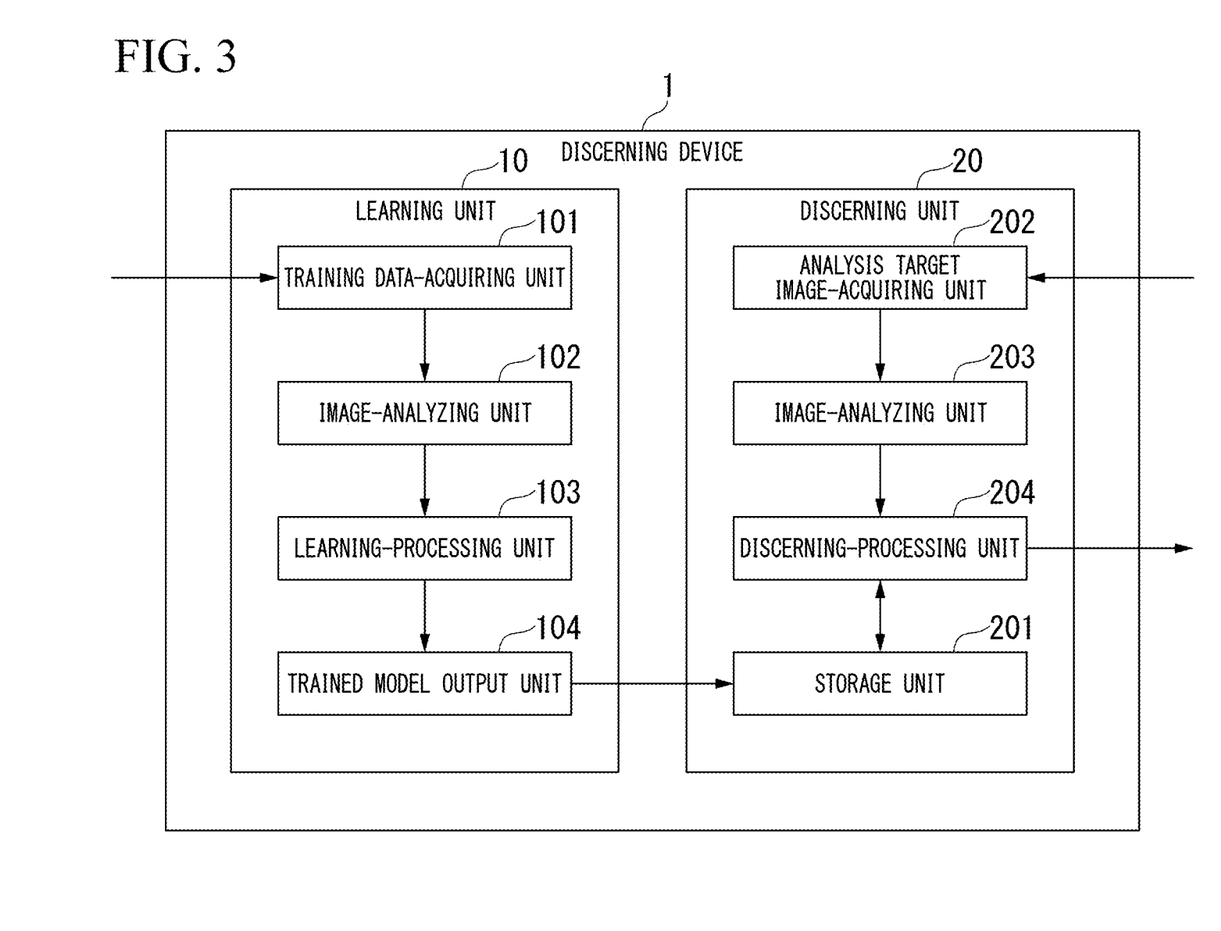
FIG. 3 is a block diagram illustrating a functional configuration of the discerning device according to the embodiment of the present invention.

FIG. 3 is a block diagram illustrating the functional configuration of the discerning device 1 according to the present embodiment.

As illustrated in FIG. 3, the discerning device 1 is configured to include a learning unit 10 and a discerning unit 20. It should be noted that in the present embodiment, both the learning unit 10 and the discerning unit 20 are functional units included in the discerning device 1, but the present invention is not limited to this configuration and the learning unit 10 and the discerning unit 20 may be functional units included in different devices.

As illustrated in FIG. 3, the learning unit 10 is configured to include a training data-acquiring unit 101, an image-analyzing unit 102, a learning-processing unit 103, and a trained model output unit 104.

The training data-acquiring unit 101 acquires a plurality of (for example, about several hundred to several thousand) pieces of training data prepared in advance for machine learning from an external device. Training data in the present embodiment is data in which an image of a cell mass (hereinafter referred to as a "training image") and a result of discerning of whether or not the cell mass is a precursor of an organoid are correlated. That is, a training image is an image of a cell mass in which it is known whether or not the cell mass is a precursor of an organoid.

Each piece of training data is generated, for example, by allowing an expert to see a cell mass appearing in an image, visually discerning whether or not the cell mass is a precursor of an organoid, and correlating the result of discerning with the image. The training data-acquiring unit 101 outputs the acquired training data to the image-analyzing unit 102.

The image-analyzing unit 102 acquires the training data output from the training data-acquiring unit 101. The image-analyzing unit 102 performs image analysis on the training image included in the training data. In the present embodiment, the image analysis performed by the image-analyzing unit 102 is to measure parameter values such as the aforementioned five parameters (Size, Circularity, Darkness, Aspect, and Roughness). The image-analyzing unit 102 inputs data (hereinafter referred to as "analyzed training data") in which five parameter values measured for the training image are correlated with the result of discerning correlated with the training image to the learning-processing unit 103.

The image-analyzing unit 102 can acquire the above parameter values by inputting the acquired training image to a convolutional neural network (CNN) which has been subjected to machine learning in advance and analyzing data (for example, a feature map or features) output from the CNN.

The learning-processing unit 103 acquires the analyzed training data output from the image-analyzing unit 102. The learning-processing unit 103 generates a trained model by performing machine learning using the analyzed training data. The learning-processing unit 103 stores the generated trained model in a storage unit 201, which will be described later, of the discerning unit 20 via the trained model output unit 104.

Specifically, the machine learning performed by the learning-processing unit 103 is learning to determine a partial regression coefficient of a logistic function with the aforementioned five indices as explanatory variables in logistic regression. A logistic function σ(t) is expressed by Expression (3).

$$\sigma(t)=1/(1+e-t) \quad (3)$$

Here, t is expressed by the following Expression (4).

$$t=w1x1+w2x2+w3x3+w4x4+w5x5+b \quad (4)$$

Here, x1, x2, x3, x4, and x5 are explanatory variables and the five parameter values which have been measured are substituted therefor. In addition, w1, w2, w3, w4, w5, and b represent partial regression coefficients to be subjected to machine learning.

Next, the discerning unit 20 will be described. As illustrated in FIG. 3, the discerning unit 20 is configured to include a storage unit 201, an analysis target image-acquiring unit 202, an image-analyzing unit 203, and a discerning-processing unit 204.

The storage unit 201 stores a trained model generated by the trained model output unit 104. As described above, the trained model is subjected to machine learning on the basis of analyzed training data (learning data) in which indices associated with a cell mass (a first cell mass) appearing in a training image out of predetermined parameters (for example, five parameters including Size, Circularity, Darkness, Aspect, and Roughness) including at least one index indicating a feature of an ROI of an analysis target image (that is, a feature of the cell mass) are correlated with information indicating whether the state of the cell mass appearing in the training image is a budding state (a first state) or a cyst state (a second state).

The storage unit 201 is configured, for example, by a storage medium such as a random-access memory (RAM: a readable writable memory), a flash memory, an electrically-erasable programmable read-only memory (EEPROM), or a hard disk drive (HDD), or an arbitrary combination of such storage media.

It should be noted that in FIG. 3, a configuration in which the discerning unit 20 includes the storage unit 201 is illustrated, but the configuration is not limited thereto and a configuration in which the learning unit 10 includes the storage unit 201 may be employed. Alternatively, a configuration in which an external device other than the discerning device 1 includes the storage unit 201 and a trained model is stored in the external device may be employed.

The analysis target image-acquiring unit 202 acquires at least one analysis target image from an external device. The analysis target image-acquiring unit 202 acquires all analysis target images generated, for example, by dividing an image acquired by imaging the inside of each well w of the well plate wp illustrated in FIG. 1 to correspond to ROIs. The analysis target image-acquiring unit 202 outputs the acquired analysis target images to the image-analyzing unit 203.

In FIG. 3, a configuration in which the analysis target image-acquiring unit 202 acquires the analysis target images from an external device is illustrated, but the present invention is not limited thereto and, for example, a configuration in which a functional unit (not illustrated) that can divide an image acquired by imaging the inside of a well w into a plurality of analysis target images is provided may be employed. Furthermore, the discerning device 1 may employ a configuration that can image the inside of a well w, for example, an imaging device (not illustrated) such as a camera and a microscope (not illustrated).

The image-analyzing unit 203 acquires analysis target images output from the analysis target image-acquiring unit 202. The image-analyzing unit 203 performs image analysis on the acquired analysis target images. In the present embodiment, the image analysis performed by the image-analyzing unit 203 is to measure the aforementioned five indices, similarly to the image analysis performed by the aforementioned image-analyzing unit 102. The image-analyzing unit 203 inputs five indices measured from each analysis target image to the discerning-processing unit 204.

It should be noted that the image-analyzing unit 203 may acquire the above indices by inputting an acquired training image to a CNN which has been subjected to machine learning in advance and analyzing data (for example, a feature map or features) output from the CNN.

It should be noted that in the present embodiment, the image-analyzing unit 102 and the image-analyzing unit 203 are independent functional units provided in the learning unit 10 and the discerning unit 20, respectively, but the present invention is not limited thereto. For example, the image-analyzing unit 102 and the image-analyzing unit 203 may be configured as a common functional unit provided in the discerning device 1.

The discerning-processing unit 204 acquires the indices output from the image-analyzing unit 203.

When the indices are acquired, the discerning-processing unit 204 reads a trained model stored in the storage unit 201. Then, the discerning-processing unit 204 inputs the acquired indices associated with a cell mass (a second cell mass) appearing in the analysis target image to the read trained model. The discerning-processing unit 204 acquires a budding rate output from the trained model in response to this input. The discerning-processing unit 204 discerns whether the state of the cell mass appearing in the analysis target image is a budding state (a first state) or a cyst state (a second state) on the basis of the acquired budding rate. The discerning-processing unit 204 outputs information indicating the result of discerning to an external device.

The discerning-processing unit 204 may output, for example, the aforementioned five indices and the value of the budding rate, instead of the information indicating the result of discerning whether the state of the cell mass is the budding state or the cyst state, as the information indicating the result of discerning. Alternatively, the discerning-processing unit 204 may output the information indicating the result of discerning whether the state of the cell mass is the budding state or the cyst state, in addition to, for example, the aforementioned five indices and the value of the budding rate. It should be noted that the discerning-processing unit 204 may output the information indicating the result of discerning to a display unit (not illustrated) such as a display provided in the discerning device 1.

Output Example of Discerning Result

Figure 4:
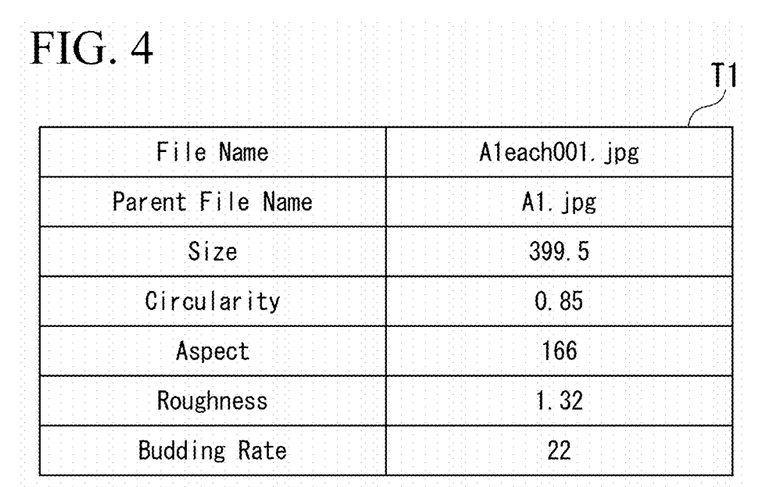
FIG. 4 is a diagram illustrating an example of indices output by the discerning device according to the embodiment of the present invention.

An output example of a discerning result from the discerning-processing unit 204 will be described below. FIG. 4 is a diagram illustrating an example of information output from the discerning device according to the present embodiment. For example, the discerning-processing unit 204 can output information indicating a discerning result in a data format such as an output table T1 illustrated in FIG. 4.

As illustrated in FIG. 4, the output table T1 is a table in which an image file name (File Name) of an analysis target image, an image file name (Parent File Name) of an image of a well w (a parent image) including the analysis target image, live indices relating to a cell mass appearing in the analysis target image, and a value of a budding rate acquired by inputting the five indices to a trained model are correlated.

The output table T1 illustrated in FIG. 4 is a table indicating a result of discerning for each ROI (that is, for each cell mass) included in an analysis target image. Moreover, for example, the discerning-processing unit 204 can output information indicating the discerning result for each of images of wells w (that is, for each well w).

Figure 5:
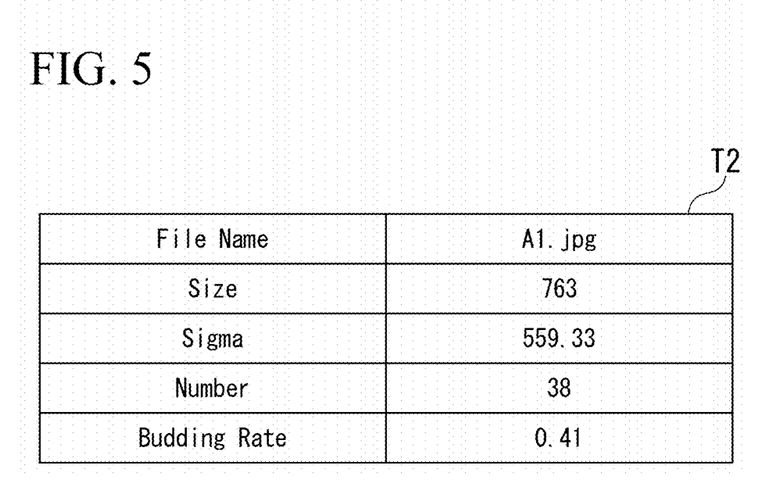
FIG. 5 is a diagram illustrating another example of the indices output by the discerning device according to the embodiment of the present invention.

FIG. 5 is a diagram illustrating another example of the information output from the discerning device 1 according to an embodiment of the present invention. For example, the discerning-processing unit 204 can output information indicating the discerning result in a data format such as an output table T2 illustrated in FIG. 5.

The output table T2 illustrated in FIG. 5 is a table in which an image file name (File Name) of an image of a well w, an average value (Size) and a standard deviation (Sigma) of the sizes of the areas (the numbers of pixels) of a plurality of ROIs included in the image of the well w, the number of cell masses (Number) included in the image of the well w, and an average value of the budding rates (Budding Rate) acquired for the plurality of cell masses included in the image of the well w are correlated.

The output table T1 illustrated in FIG. 5 is a table indicating a discerning result for each image of a well w (a parent image) (that is, for each well w). It should be noted that for example, the discerning-processing unit 204 can output information indicating the discerning result for each well plate wp illustrated in FIG. 1.

[Operation of Learning Unit]

The operation of the learning unit 10 will be described below.

Figure 6:
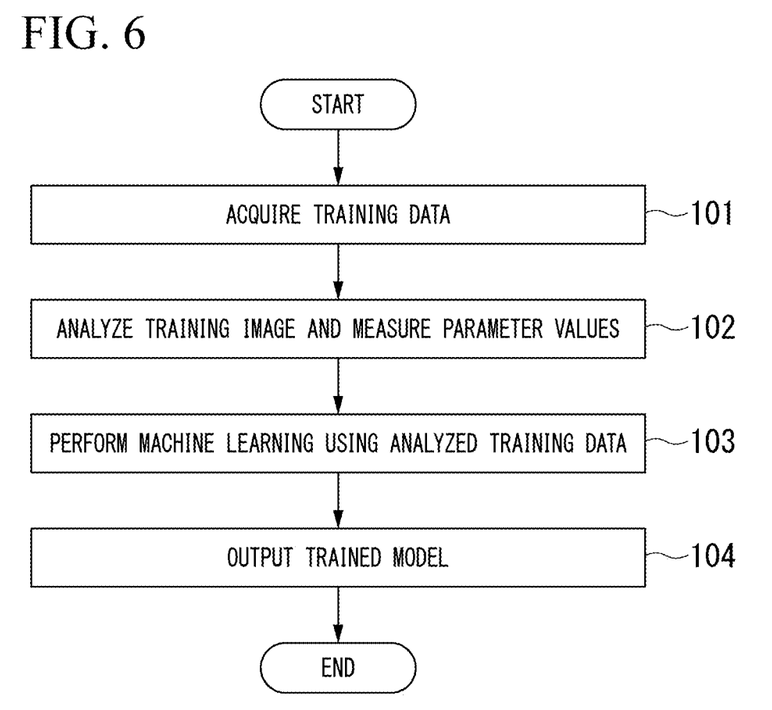
FIG. 6 is a flowchart illustrating an operation of a learning unit 10 of the discerning device 1 illustrated in FIG. 3.

FIG. 6 is a flowchart illustrating the operation of the learning unit 10 of the discerning device 1 illustrated in FIG. 3. The operation of the learning unit 10 illustrated in this flowchart is started when training data prepared in advance for machine learning is input to the training data-acquiring unit 101.

The training data-acquiring unit 101 receives the input training data, which is data in which a training image and a result of discerning whether or not a cell mass is a precursor of an organoid are correlated (Step S101). The training data-acquiring unit 101 outputs the input training data to the image-analyzing unit 102.

The image-analyzing unit 102 receives the training data output from the training data-acquiring unit 101. The image-analyzing unit 102 performs image analysis on the training image included in the training data and measures the aforementioned five indices (Step S102). The image-analyzing unit 102 outputs analyzed training data which is data in which the five indices measured for a cell mass appearing in the training image are correlated with a discerning result correlated with the training image to the learning-processing unit 103.

The learning-processing unit 103 receives the analyzed training data output from the image-analyzing unit 102. The learning-processing unit 103 executes machine learning using the analyzed training data (Step S103). As a result, a trained model is generated. The learning-processing unit 103 outputs the generated trained model to the storage unit 201 of the discerning unit 20 (Step S104). Then, the operation of the learning unit 10 illustrated in the flowchart of FIG. 6 ends.

[Operation of Discerning Unit]

The operation of the discerning unit 20 will be described below.

Figure 7:
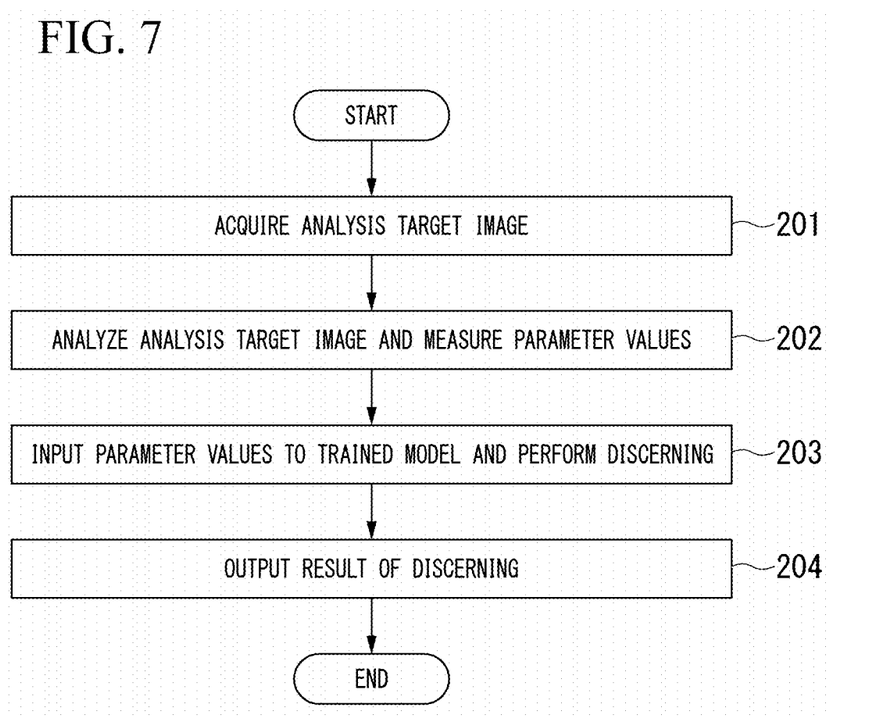
FIG. 7 is a flowchart illustrating an operation of a discerning unit 20 of the discerning device 1 illustrated in FIG. 3.

FIG. 7 is a flowchart illustrating the operation of the discerning unit 20 of the discerning device 1 illustrated in FIG. 3. The operation of the discerning unit 20 illustrated in this flowchart is started when at least one analysis target image is input to the analysis target image-acquiring unit 202 of the discerning unit 20.

The analysis target image-acquiring unit 202 receives an analysis target image (Step S201). The analysis target image-acquiring unit 202 outputs the analysis target image to the image-analyzing unit 203.

The image-analyzing unit 203 receives the analysis target image output from the analysis target image-acquiring unit 202. The image-analyzing unit 203 analyzes the acquired analysis target image and measures the aforementioned five indices (Step S202). The image-analyzing unit 203 outputs the indices measured for a cell mass appearing in the analysis target image to the discerning-processing unit 204.

The discerning-processing unit 204 receives the indices output from the image-analyzing unit 203. When the indices are received, the discerning-processing unit 204 reads a trained model stored in the storage unit 201. Then, the discerning-processing unit 204 inputs the acquired indices associated with the cell mass appearing in the analysis target image to the read trained model. The discerning-processing unit 204 acquires a value of a budding rate output from the trained model in response to an input of the parameter values. The discerning-processing unit 204 executes discerning whether the state of the cell mass appearing in the analysis target image is the budding state or the cyst state (that is, whether or not the cell mass appearing in the analysis target image is a precursor of an organoid) on the basis of the acquired value of the budding rate (Step S203).

The discerning-processing unit 204 outputs information indicating the discerning result to an external device (Step S204). Then, the operation of the discerning unit 20 illustrated in the flowchart of FIG. 7 ends.

EXAMPLES

Example 1

Examples will be described below. However, the present invention is not limited to the following examples at all.

1) Intestinal organoids were cultured using a 48-well plate (a culturing method thereof is arbitrary and thus specific description thereof is omitted).

2) Bright-field transmission images of organoids cultured in the 48-well plate were imaged for each well using an inverted microscope (BZ-X710) made by KEYENCE CORPORATION. Images with a resolution of 1980×1440 were acquired with a quick full focus function using a CFI Plan Apoλ2x as an objective lens.

3) The organoids were recognized one by one by setting an appropriate threshold value using an OpenCV-Python library, and organoid ranges of the organoids were taken out one by one as regions of interest (ROIs) from the captured images of the inside of the wells.

4) (Extraction of features) Five features (Size, Circularity, Darkness, Aspect, and Roughness) for each taken-out ROI were calculated as follows.

Size: The number of pixels included in an ROT was counted using the OpenCV-Python library.

Circularity: The circularity was calculated using Expression (1) from the diameter (or radius) S and a circumference length Per of an ROI.

Darkness: The darkness was calculated using Expression (2) from an average value of luminance Bo (256 gray scales) around an ROI and an average value of luminance Bi (256 gray scales) inside the ROI.

Aspect: A longest axis and a shortest axis were selected out of major axes and minor axes of an ROI and the Aspect was calculated using an expression (long-axis length/short-axis length).

Roughness: Edges of an ROI were detected using the Canny method and the number of detected edges was calculated.

[Learning]

5) Data in which the five features extracted from a cell mass and information indicating whether or not culture of an organoid for the cell mass was successful (success was set to "1" and failure was set to "0") were correlated was prepared for 1000 cell masses. Then, logistic regression analysis based on above Expression (3) and Expression (4) was performed on the basis of the data. As a result, a regression expression in which the following appropriate weights were assigned to the partial regression coefficients of a logistic function was obtained.

w1=0.00198
w2=−5.03
w3=0.260
w4=0.124
w5=−0.00723
b=−42.5

[Prediction]

6) The five features were extracted from an image of a new cell mass and a success probability in culturing an organoid for the cell mass was calculated by substituting the extracted features for the regression expression obtained in 5) above.

7) A success probability of one well was calculated by collecting the organoids included in the well and calculating an arithmetic mean of the success probabilities in culturing of the organoids.

[Discerning Accuracy]

8) An accuracy rate was calculated on the basis of the success probability calculated in 7) above and actual success in culturing of the organoids. As a result, an accuracy rate of 81.1% was obtained.

Example 2

9) For the purpose of comparison with implementation conditions described above in 4), logistic regression analysis based on Expression (3) and Expression (4) above was performed using only one to four variables out of the aforementioned five variables and using data for 1000 cell masses. As a result, the result that the discerning accuracy was highest when the five variables described above in 4) were used was obtained.

As described above, the discerning unit 20 of the discerning device 1 according to the embodiment illustrated in FIG. 3 is configured to include the storage unit 201 and the discerning-processing unit 204. The storage unit 201 stores a trained model which has been subjected to machine learning on the basis of analyzed training data (learning data) in which index values associated with a cell mass (a first cell mass) appearing in a training image out of predetermined indices including at least one index indicating features of a cell mass and information indicating whether the state of the cell mass appearing in the training image is the budding state (the first state) or the cyst state (the second state) are correlated.

Moreover, the discerning-processing unit 204 acquires indices associated with a cell mass (a second cell mass) appearing in an analysis target image out of the predetermined indices and discerns whether the state of the cell mass appearing in the analysis target image is the budding state (the first state) or the cyst state (the second state) on the basis of the budding rate output in response to an input of parameter values associated with the cell mass appearing in the input analysis target image to the trained model stored in the storage unit 201.

By employing the aforementioned configuration, the discerning device 1 according to the aforementioned embodiment can quantitatively discern whether or not a cell mass is a precursor of an organoid.

Moreover, the discerning device 1 according to the embodiment illustrated in FIG. 3 can automatically discern whether or not a cell mass is a precursor expected to be an organoid using a trained model, unlike visual discerning by an expert. Accordingly, with the discerning device according to the present embodiment, even when an expert who can perform the discerning is absent, it is possible to easily discern whether or not a cell mass is a precursor of an organoid. Moreover, since the discerning device according to the present embodiment can automatically perform the discerning using a trained model, it is possible to perform faster discerning at a lower cost.

Moreover, since the discerning device 1 according to the embodiment illustrated in FIG. 3 can automatically perform the discerning using a trained model, it is possible to perform discerning for a shorter time, for example, even when the discerning is performed on a large number of organoids included in a well w.

Moreover, since the discerning device 1 according to the embodiment illustrated in FIG. 3 can quantitatively discern whether or not a cell mass is a precursor of an organoid, it is also possible to perform discerning for each well w or for each well plate wp, for example, by calculating an average value of the values of the budding rates.

Moreover, since the discerning device 1 according to the embodiment illustrated in FIG. 3 discerns whether or not a cell mass is a precursor of an organoid using a trained model, it is possible to perform the discerning with less indices, for example, in comparison with the related art in which various types of indices need to be measured as in the technique described in Non-Patent Literature 1. Accordingly, it is possible to decrease the costs and time for measurement of indices.

It should be noted that in the embodiment illustrated in FIG. 3, the discerning device 1 is a device that discerns whether or not a cell mass is a precursor of an organoid, but the present invention is not limited thereto. For example, the discerning device 1 illustrated in FIG. 3 can also be applied to discerning of the state of a cell mass performed to determine a timing at which cultured organoids are harvested, discerning of whether or not a harvested organoid is an organoid which has grown normally, or the like.

It should be noted that part of or entirety of the discerning device 1 according to the embodiment illustrated in FIG. 3 may be realized by a computer. In this case, it may be realized by recording a program for realizing control functions thereof on a computer-readable recording medium and causing a computer system to read and execute the program recorded on the recording medium. It should be noted that the "computer system" mentioned here is a computer system incorporated in the discerning device 1 and includes an OS and hardware such as peripheral devices. Moreover, the "computer-readable recording medium" is a portable medium such as a flexible disk, a magneto-optical disc, a ROM, or a CD-ROM or a storage device such as a hard disk incorporated in a computer system. Furthermore, the "computer-readable recording medium" may include a medium that dynamically holds a program for a short time like a communication circuit when a program is transmitted via a network such as the Internet or a communication circuit such as a telephone circuit, or a medium that holds a program for a predetermined time like a volatile memory inside a computer system which serves as a server or a client in that case. Moreover, the program may be a program for realizing some of the aforementioned functions, or may also be a program for realizing the aforementioned functions in combination with a program already stored in the computer system.

Moreover, the discerning device 1 according to the embodiment illustrated in FIG. 3 may be realized as an integrated circuit such as large-scale integration (LSI). The functional blocks of the discerning device 1 may be individually formed as processors or some or all thereof may be integrated and formed as a processor. Moreover, the technique of forming an integrated circuit is not limited to LSI and they may be realized as a dedicated circuit or a general-purpose processor. Moreover, when a technique of forming an integrated circuit that replaces the LSI appears with advancement in semiconductor technology, an integrated circuit based on this technology may be used.

While an embodiment of the present invention has been described above with reference to the drawings, it is apparent that the above embodiment is only an example of the present invention and the present invention is not limited to the above embodiment. Therefore, addition, omission, replacement, and other modifications may be performed without departing from the technical idea and the gist of the present invention.

What is claimed is:

1. A discerning device that discerns a cell mass, the discerning device comprising:
    storage circuitry configured to store a trained model that has been subjected to machine learning on the basis of training data in which an index value associated with a first cell mass out of a predetermined index including at least one index selected from size, circularity, darkness, aspect, and roughness is correlated with information indicating whether a state of the first cell mass is a budding state or a cyst state, the index value indicating a feature of the first cell mass obtained from a static image at a point in time when the first cell mass was imaged;
    image-analyzing circuitry configured to acquire an index value associated with a second cell mass out of the predetermined index; and
    discerning-processing circuitry configured to discern whether a state of the second cell mass is the budding state or the cyst state on the basis of the index value associated with the second cell mass and the trained model.

2. The device of claim 1, wherein the predetermined index includes an index indicating complexity of a shape of the cell mass.

3. The device of claim 1, wherein the machine learning is learning to determine a partial regression coefficient of a logistic function with the predetermined index as an explanatory variable.

4. The device of claim 3, wherein the machine learning is learning to determine the partial regression coefficient of the logistic function with each of a plurality of index values.

5. The device of claim 1, further comprising: image-acquiring circuitry configured to transmit an image in which the second cell mass is captured to the image-analyzing circuitry.

6. The device of claim 5, wherein the image-analyzing circuitry is further configured to
    detect edges of the second cell mass from the image using the Canny method, and
    measure an index indicating complexity of a shape of the cell mass on the basis of the number of detected edges.

7. The device of claim 1, wherein the static image is a bright-field transmission image.

8. The device of claim 1, wherein the static image is divided in units of cell mass.

9. The device of claim 1, wherein the static image is divided for each region of interest recognized in an image including the cell mass which is to be an organoid.

10. The device of claim 1, wherein the discerning-processing circuitry is configured to
    calculate a budding rate value indicating a probability that the state of the second cell mass is the budding state by inputting the index value into the trained model, and
    determine whether the state of the second cell mass is the budding state or the cyst state based on the calculated budding rate value.

11. The device of claim 10, wherein the discerning-processing circuitry is configured to
    divide the static image into a plurality of analysis target images including the cell mass,
    calculate the banding rate value of the second cell mass in each of the plurality of analysis target images,
    calculate an average value of banding rate values of the plurality of analysis target images included in the static image, and
    determine whether a state of the static image is the banding state or the cyst state based on the calculated average value.

12. A method of discerning a cell mass that is performed by a computer, the method comprising:
    acquiring a trained model that has been subjected to machine learning on the basis of training data in which an index value associated with a first cell mass out of a predetermined index including at least one index selected from size, circularity, darkness, aspect, and roughness is correlated with information indicating whether a state of the first cell mass is a budding state or a cyst state, the index value indicating a feature of the first cell mass obtained from a static image at a point in time when the first cell mass was imaged;
    acquiring an index value associated with a second cell mass out of the predetermined index; and
    discerning whether a state of the second cell mass is the budding state or the cyst state on the basis of the acquired index value associated with the second cell mass and the trained model.

13. A non-transitory computer-readable storage medium including computer executable instructions, wherein the instructions, when executed by a computer, cause the computer to perform a method of a cell mass, the method comprising:
    acquiring a trained model that has been subjected to machine learning on the basis of training data in which an index value associated with a first cell mass out of a predetermined index including at least one index selected from size, circularity, darkness, aspect, and roughness is correlated with information indicating whether a state of the first cell mass is a budding state or a cyst state, the index value indicating a feature of the first cell mass obtained from a static image at a point in time when the cell mass was imaged:
    acquiring an index value associated with a second cell mass out of the predetermined index; and
    discerning whether a state of the second cell mass is the budding state or the cyst state on the basis of the acquired index value associated with the second cell mass and the trained model.

* * * * *